US012691152B2

(12) United States Patent
He

(54) MEDICINE FOR TOPICAL WOUND TREATMENT

(71) Applicant: kesaisi (Hainan) Technology Co., Ltd., Haikou (CN)

(72) Inventor: Xiaojie He, Changsha (CN)

(73) Assignee: KESAISI (HAINAN) TECHNOLOGY CO., LTD., Haikou (CN)

( * ) Notice: Subject to any disclaimer, the term of this patent is extended or adjusted under 35 U.S.C. 154(b) by 277 days.

(21) Appl. No.: 18/424,754

(22) Filed: Jan. 27, 2024

(65) Prior Publication Data

US 2025/0205295 A1    Jun. 26, 2025

(30) Foreign Application Priority Data

Dec. 21, 2023    (CN) ........................ 202311778635.X

(51) Int. Cl.
| | |
|---|---|
| *A61K 36/185* | (2006.01) |
| *A61K 9/00* | (2006.01) |
| *A61K 36/22* | (2006.01) |
| *A61K 36/28* | (2006.01) |
| *A61K 36/288* | (2006.01) |
| *A61K 36/52* | (2006.01) |
| *A61K 36/81* | (2006.01) |
| *A61K 36/82* | (2006.01) |
| *A61P 17/02* | (2006.01) |

(52) U.S. Cl.
CPC ........... *A61K 36/22* (2013.01); *A61K 9/0014* (2013.01); *A61K 36/185* (2013.01); *A61K 36/28* (2013.01); *A61K 36/288* (2013.01); *A61K 36/52* (2013.01); *A61K 36/81* (2013.01); *A61K 36/82* (2013.01); *A61P 17/02* (2018.01);

(10) Patent No.: US 12,691,152 B2
(45) Date of Patent: Jul. 28, 2026

*A61K 2236/13* (2013.01); *A61K 2236/15* (2013.01); *A61K 2236/33* (2013.01); *A61K 2236/39* (2013.01); *A61K 2236/51* (2013.01)

(58) Field of Classification Search
CPC .... A61K 36/22; A61K 9/0014; A61K 36/185; A61K 36/28; A61K 36/288; A61K 36/52; A61K 36/81; A61K 36/82; A61K 2236/13; A61K 2236/15; A61K 2236/33; A61K 2236/39; A61K 2236/51; A61K 2236/333; A61K 2236/55; A61K 36/232; A61K 36/287; A61K 36/62; A61K 9/19; A61K 35/64; A61P 17/02; A61P 3/10
See application file for complete search history.

(56) References Cited

PUBLICATIONS

Honda, Shinsuke. "Method For Preparing Hair Growth Agent, And Composition Prepared By Said Method". TW 201338789 A, filed Dec. 17, 2012 and published Oct. 1, 2013—English translation. (Year: 2013).*

* cited by examiner

*Primary Examiner* — Susan Hoffman
*Assistant Examiner* — Nashara L Moreau
(74) *Attorney, Agent, or Firm* — Hemisphere Law, PLLC

(57) ABSTRACT

A medicine for topical wound treatment relates to the field of pharmaceutical technology. A plant composition incudes tea leaves, lotus leaves, *Galla chinensis, Stevia rebaudiana, Cyclocarya paliurus, Gynura divaricata, Taraxacum mongolicum* and *Solanum lycopersicum*. The medicine for topical wound treatment can promote the rapid repair of diabetic foot ulcers (DFUs) and reduce the damage of the DFUs to human health by controlling the local blood glucose, local infection, microvascular injury, inflammatory reaction, peripheral nerve injury, coagulation-hemolysis dysfunction of the DFUs.

4 Claims, 4 Drawing Sheets

MEDICINE FOR TOPICAL WOUND TREATMENT

TECHNICAL FIELD

The disclosure relates to the field of pharmaceutical technologies, and particularly to a medicine for topical wound treatment.

BACKGROUND

Diabetic patients are at risk of developing foot ulcers. Diabetic foot ulcers (DFUs), also known as diabetic foot, are one of the main complications of diabetes. The size of the patient population with DFUs is enormous, with high mortality and disability rates.

The reason why diabetic wounds are difficult to heal is the result of interactions between endogenous changes of nerves, blood vessels, immunity, metabolism and pathogenic factors such as infection and trauma, stress. First, the continuous activation of glucose polyol metabolic pathway in diabetic patients can lead to a large amount of sorbitol accumulation in nerve tissue cells and cause neuropathy. Secondly, sustained high blood glucose can also cause endothelial dysfunction (also referred to as endothelial cell dysfunction), which leads to the release of nitric oxide (NO). On the one hand, nitric oxide can reduce the angiogenesis of the wound, on the other hand, nitric oxide can significantly reduce the vasodilation function of blood vessels by relaxing the smooth muscle, leading to lower limb ischemia or nerve ischemia. In addition, neuropathy, local blood flow insufficiency, and high blood glucose can cause damage to leucocytes and immune function, which leads to insufficient inflammatory response in wound tissue. As a result, the DFUs of the patients appear to be healing, but turn out to be an effective pathway for infection, eventually causing sepsis and amputation.

DFUs are often the gateway to bacterial infections, causing a large number of neutrophils, monocytes, and macrophages to infiltrate the wound, thereby forming granulation tissue. When a large number of leucocytes are present in wound infection, the leucocytes release toxic proteolytic enzymes and free radicals, causing tissue damage, reducing production of growth factors, reducing the number of deposition of fibroblasts, and disrupting the arrangement of collagen. The diabetic patients need a longer time for wound healing, mainly because the physiological processes such as angiogenesis, inflammatory response, expression of connexin, matrix metalloproteinases (MMPs) and abnormal immune response cannot be carried out orderly.

At present, the commonly accepted view on the mechanism of DFUs is the ternary theory of DFUs: diabetic neuropathy, ischemic disease of diabetes, and local infection of diabetes are the three most important risk factors as the basis, and external minor trauma as the inducement can promote the formation and development of ulcers.

The ischemic disease of diabetes is caused by both macroangiopathy and microangiopathy. The characteristics of peripheral vascular disease in diabetic patients are as follows: many diabetic patients have no obvious symptom of diabetes, but severe ischemia of lower limbs is often the first symptom of diabetes. The peripheral vascular disease in diabetic patients is a sign of macroangiopathy of systemic organs, such as the heart, brain, and kidney. The peripheral vascular disease increases the incidence of endpoint events. In this situation, the diabetic patients are much higher than those without diabetes to suffer endpoint events. The pathological characteristics of the macroangiopathy in diabetic patients are as follows: intimal atherosclerosis and Monckeberg's arteriosclerosis. The macroangiopathy invade main arteries with a diameter greater than 2 millimeters (mm), such as blood vessels below the popliteal fossa and pedis artery. The pathological and clinical characteristics of the microangiopathy in diabetic patients are as follows: thickening of capillary basement membrane and impaired nutrient exchange, but no intravascular embolism. Due to opening of arteriovenous (A-V) shunt caused by autonomic neuropathy, blood flow is 5 times higher than normal, and the temperature regulation mechanism is impaired.

The diabetic neuropathy is the most common complication of diabetes. The diabetic neuropathy has various symptoms, which can affect sensory, motor and autonomic nerves, sometimes with a mixture of lesions. The diabetic neuropathy is a serious complication threatening the lower limbs and can lead to secondary ulcers, infections and gangrene, resulting in amputation and Charcot arthropathy (also known as Charcot neuroarthropathy or Charcot foot and ankle). Sensory neuropathy can cause sensory disturbance or painful neuropathy. The loss of neurotrophic function can cause claw toe, atrophy of calf muscles, foot drop, gait changes (also referred to as abnormal gait), and atrophy of gastrocnemius muscle. Autonomic neuropathy causes changes such as no sweat, dry skin, no fine hair, and opening of arteriovenous shunt. Neuropathy can also cause changes in the shape of foot, that is, foot deformity. The foot deformity is very common in diabetic patients. Idiopathic foot deformities include toe deformities, claw toes, hallux valgus, hammer toes, and metatarsophalangeal deformities. The neuropathy can not only cause various foot deformities mentioned above but also lead to arthropathy. After amputation surgery, the neuropathy can also cause secondary foot deformities and foot deformities are prone to secondary pressure injuries.

Compared with non-diabetic patients, the incidence of diabetic foot infections (DFIs) in the diabetic patients is higher. The incidence of various infections in the diabetic patients is 21% higher than that in non-diabetic patients. Foot infections are often caused by trauma and are an important threat to the lower limbs, which are related to ulcers and can often lead to amputation. The immunological causes of the DFUs are abnormal host responses, including abnormal function of neutrophils, abnormal chemical chemotaxis responses, abnormal function of macrophages, and abnormal bactericidal ability.

Currently, the commonly used treatment methods for DFUs include wound debridement, dressing, foot pressure release, antibiotics infection control, blood glucose control, and control of peripheral vascular disease. (Lu Tie, Yilixiati Xiaokaiti, Xian Wang et al., Molecular mechanisms of diabetic wound healing, Progress in Physiological Sciences, 2010, pages 9-14). However, the clinical effects of those method are not very satisfactory.

Tea polyphenols are a general term of phenolic substances and their derivatives in tea, accounting for about 20% to 35% of the total amount of the tea, including flavanols, anthocyanins, flavonoids, flavonols, and phenolic acids. Among them, the flavanols (catechins) are the most important, and they have good effects in inhibiting bacteria, anti-inflammation, antioxidant, regulating blood pressure, reducing vascular damage, and inhibiting the development of atherosclerosis. Procyanidin not only has antioxidant effects, but also has microvascular regeneration function. Vitamin C (also referred to as ascorbic acid) can improve vascular fragility. *Galla chinensis* extract abbreviated as GCE) (polyphenolic compounds) has antibacterial, anti-inflammatory, and antioxidant effects. Extracts of *Stevia rebaudiana* and *Cyclocarya paliurus* have the effect of reducing local blood glucose levels.

It can be seen that the above several plant functional components have antioxidant, antibacterial and anti-inflammatory effects, hypoglycemic effects, and antagonistic effects on vascular injury. However, each functional component only has its specific biological function in a certain aspect. At present, the research at home and abroad is only limited to the research of the biological action mechanism of a single functional component, which lacks the research on the synergistic effect of multiple plant functional components in the treatment of a certain disease. In the process of the occurrence and development of DFUs, it is often accompanied by neuropathy, ischemic disease of diabetes and local infections. Therefore, in the clinical treatment of DFUs, when lowering blood glucose, it is usually necessary to control the local blood glucose, local infection, microvascular injury, inflammatory response, peripheral nerve injury, and coagulation-hemolysis dysfunction of the DFUs for comprehensive treatments. Therefore, it is urgent to study physiological effects of various functional components in the treatment of diseases.

SUMMARY

In view of the shortcomings of the related art, the disclosure provides a medicine for topical wound treatment, which can promote the rapid repair of diabetic foot ulcers (DFUs) and reduce the damage of the DFUs to human health by controlling the local blood glucose, local infection, microvascular injury, inflammatory response, peripheral nerve injury, coagulation-hemolysis dysfunction of the DFUs.

In order to achieve above purpose, the disclosure is implemented through the following technical solutions.

Specifically, in an aspect, a plant composition for wound treatment (i.e., a plant composition for treating wounds) is provided and includes tea leaves, lotus leaves, *Galla chinensis, Stevia rebaudiana, Cyclocarya paliurus, Gynura divaricata, Taraxacum mongolicum* and *Solanum lycopersicum*.

In an embodiment, a mass percentage of the tea leaves is in a range of 10%-40%, a mass percentage of the lotus leaves is in a range of 9%-30%, a mass percentage of the *Galla chinensis* is in a range of 9%-20%, a mass percentage of the *Stevia rebaudiana* is in a range of 9%-20%, a mass percentage of the *Cyclocarya paliurus* is in a range of 9%-20%, a mass percentage of the *Gynura divaricata* is in a range of 9%-20%, a mass percentage of the *Taraxacum mongolicum* is in a range of 9%-20% and a mass percentage of the *Solanum lycopersicum* is in a range of 5%-20%.

In another aspect, a preparation method of a plant extract using the plant composition is as follows:

step (1), crushing a mixture of the tea leaves, the lotus leaves, the *Galla chinensis*, the *Stevia rebaudiana*, the *Cyclocarya paliurus*, the *Gynura divaricata*, the *Taraxacum mongolicum* and the *Solanum lycopersicum* prepared according to a ratio to obtain a crushed mixture, wrapping the crushed mixture in a gauze and adding sodium carbonate ($NaCO_3$) to obtain a mixture to be treated, followed by boiling the mixture to be treated with ethanol to collect a first extraction solution, than washing the gauze wrapped with the mixture after the boiling multiple times using the ethanol to obtain a washing solution, and adding the washing solution into the first extraction solution to obtain a first target extraction solution;

step (2), concentrating the first target extraction solution to obtain a concentrated extraction solution, cooling the concentrated extraction solution to a room temperature, performing fluid extraction 1-3 times on the concentrated extraction solution after cooling with chloroform to obtain a second extraction solution and an aqueous layer, extracting the aqueous layer 1-3 times with ethyl acetate to obtain an extraction solution of the aqueous layer, and combining the second extraction solution and the extraction solution of the aqueous layer to obtain a second target extraction solution; and step (3), distilling the second target extraction solution under a reduced pressure until the second target extraction solution is concentrated to be a solid extract, cooling the solid extract to a room temperature, and freeze-drying the solid extract after cooling to obtain the plant extract in a form of powder.

In an embodiment, a mass ratio of the crushed mixture to the sodium carbonate is in a range of 5-10:1-2.

In an embodiment, the plant extract includes an extract of the tea leaves, an extract of the lotus leaves, an extract of the *Galla chinensis*, an extract of the *Stevia rebaudiana*, an extract of the *Cyclocarya paliurus*, an extract of the *Gynura divaricata*, an extract of the *Taraxacum mongolicum* and an extract of the *Solanum lycopersicum*.

In still another aspect, an application method of the plant composition includes: preparing a medicine for topical wound treatment by using the plant composition to treat wounds.

In an embodiment, the plant composition is applied to treat DFU.

In even still another aspect, an application method of the plant extract includes: administering the plant extract to a patient with DFU to perform topical wound treatment.

The beneficial effects of the disclosure are as follows.

In the disclosure, tea polyphenols (tea leaves), procyanidin (lotus leaves), the extract of the *Galla chinensis*, the extract of the *Stevia rebaudiana*, the extract of the *Cyclocarya paliurus*, the extract of the *Gynura divaricata*, the extract of the *Taraxacum mongolicum*, and the appropriate amount of *Solanum lycopersicum* (ascorbic acid also referred to as vitamin C) are added together to prepare the topical therapeutic medicine for treating DFUs. The medicine can promote the rapid repair of the DFUs and reduce the damage of the DFUs to human health by controlling the local blood glucose, local infection, microvascular injury, inflammatory reaction, peripheral nerve injury, coagulation-hemolysis dysfunction of the DFUs.

DETAILED DESCRIPTION OF EMBODIMENTS

Figure 1:
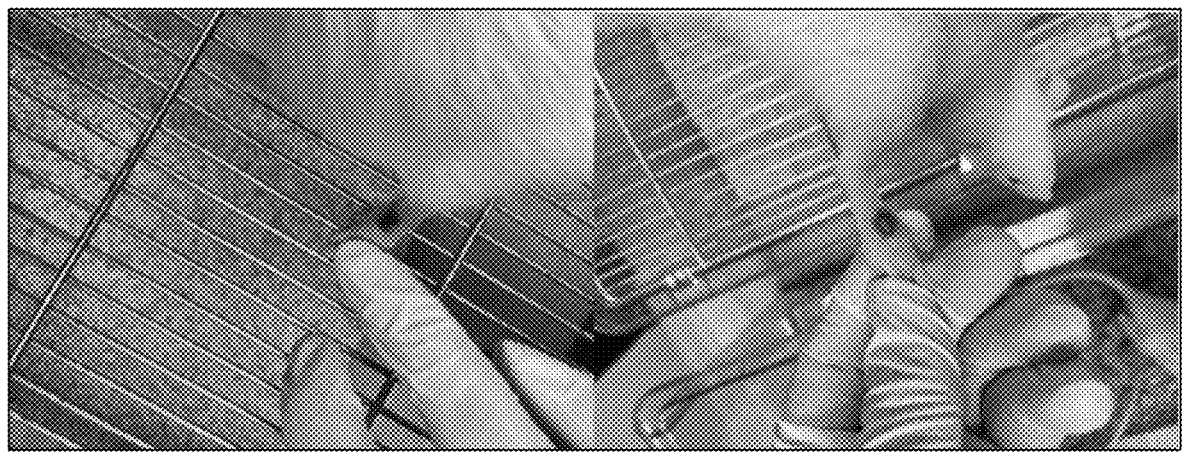
FIG. 1 illustrates a modeling diagram of rats treated with a suspension of *Staphylococcus aureus*.

The following will provide a clear and complete description of the technical solution in the embodiments of the disclosure, in conjunction with the attached drawings. Apparently, the described embodiments are only a part of the embodiments of the disclosure, not all of them. Based on the embodiments in the disclosure, all other embodiments obtained by those skilled in the art without creative labor fall within the scope of protection of the disclosure.

If not specifically specified, the technical means used in the embodiments are conventional means well-known to those skilled in the art.

1. The disclosure provides a plant composition for wound treatment (i.e., a plant composition for treating wounds), including: tea leaves, lotus leaves, *Galla chinensis, Stevia rebaudiana, Cyclocarya paliurus, Gynura divaricata, Taraxacum mongolicum* and *Solamum lycopersicum.*

A mass percentage of the tea leaves is in a range of 10%-40%, a mass percentage of the lotus leaves is in a range of 9%-30%, a mass percentage of the *Galla chinensis* is in a range of 9%-20%, a mass percentage of the *Stevia rebaudiana* is in a range of 9%-20%, a mass percentage of the *Cyclocarya paliurus* is in a range of 9%-20%, a mass percentage of the *Gymra divaricata* is in a range of 9%-20%, a mass percentage of the *Taraxacum mongolicum* is in a range of 9%-20% and a mass percentage of the *Solamum lycopersicum* is in a range of 5%-20%.

2. A preparation method of a plant extract using the plant composition includes steps as follows.

(1) Liquid extraction: a mixture of the tea leaves, the lotus leaves, the *Galla chinensis*, the *Stevia rebaudiana*, the *Cyclocarya paliurus*, the *Gynura divaricata*, the *Taraxacum mongolicum* and the *Solanum lycopersicum* prepared according to a ratio is crushed to obtain a crushed mixture, then the crushed mixture is wrapped in a gauze and added sodium carbonate to obtain a mixture to be treated, followed by placing the mixture to be treated into a 3-neck flask and adding 50-80 millimeters (mL) of absolute alcohol to boil the mixture to be treated for 0.5-2 hours (h), thereby obtaining a first extraction solution, and the first extraction solution is collected into an evaporating dish. The gauze wrapped with the mixture after boiling is washed 1-2 times using 10-30 mL of the ethanol to further collect a washing solution into the evaporating dish, thereby obtaining a first target extraction solution. A mass ratio of the crushed mixture to the sodium carbonate is in a range of 5-10:1-2.

(2) Separation and purification: the evaporating dish with the first target extraction solution is placed on an asbestos mesh (also referred to as heat-resistant wire mesh) and heated to concentrate the first target extraction solution to obtain a concentrated extraction solution with a volume of about 20-40 mL. After cooling the concentrated extraction solution to a room temperature, the concentrated extraction solution is transferred to a separating funnel and added with chloroform equaled to an amount of the concentrated extraction solution for fluid extraction 2-3 times (shake gently during extraction to prevent emulsification), thereby obtaining a second extraction solution and an aqueous layer. The aqueous layer is used to prepare the extract.

After the fluid extraction with the chloroform, the aqueous layer is extracted by using ethyl acetate equaled to an amount of the aqueous layer for 2-3 times, each time for 20-40 minutes, thereby obtaining an extraction solution of the aqueous layer (i.e., ethyl acetate extract liquid). Then the ethyl acetate in the extraction solution of the aqueous layer is collected from the extraction solution of the aqueous layer through water bath vacuum distillation (or rotary evaporator), thereby obtaining a raffinate solution. The raffinate solution is transferred into a clean and dry evaporating dish when the raffinate solution is hot, followed by using a steam bath to heat and concentrate until the raffinate solution is almost dry, thereby obtaining a solid extract. After cooling the solid extract to a room temperature, the solid extract is freeze-dried to obtain a crude powder extract (i.e., plant extract). The crude powder extract includes the extract of the tea leaves, the extract of the lotus leaves, the extract of the *Galla chinensis*, the extract of the *Stevia rebaudiana*, the extract of the *Cyclocarya paliurus*, the extract of the *Gynura divaricata*, the extract of the *Taraxacum mongolicum* and the extract of the *Solanum lycopersicum.*

In an embodiment, the extract of the tea leaves is tea polyphenols, the extract of the lotus leaf is procyanidin, and the extract of the *Solanum lycopersicum* is ascorbic acid (also referred to as vitamin C).

3. An application of the plant extract as a medicine for topical wound treatment (i.e., as a medicine used externally for wound treatment) in the wound treatment. The plant extract is applied to treat diabetic foot ulcer (DFU).

The disclosure will be further limited in combination with specific embodiments below.

Embodiments 1-5

Multiple groups of therapeutic medicines are prepared according to the above formulation with specific ratios shown in Table 1 below.

TABLE 1

| Ratios of respective embodiments | |
| --- | --- |
| Embodiments | Formulation (mass percentage) |
| 1 | tea leaves (30%), lotus leaves (15%), *Galla chinensis* (10%), *Stevia rebaudiana* (10%), *Cyclocarya paliurus* (10%), *Gynura divaricata* (10%), *Taraxacum mongolicum* (10%), *Solanum lycopersicum* (5%) |
| 2 | tea leaves (20%), lotus leaves (15%), *Galla chinensis* (15%), *Stevia rebaudiana* (10%), *Cyclocarya paliurus* (15%), *Gynura divaricata* (10%), *Taraxacum mongolicum* (10%), *Solanum lycopersicum* (5%) |
| 3 | tea leaves (25%), lotus leaves (15%), extract of *Galla chinensis* (15%), extract of *Stevia rebaudiana* (10%), extract of *Cyclocarya paliurus* (10%), |

TABLE 1-continued

| Ratios of respective embodiments | |
| --- | --- |
| Embodiments | Formulation (mass percentage) |
| | extract of *Gynura divaricata* (10%), extract of *Taraxacum mongolicum* (10%), extract of *Solanum lycopersicum* (5%) |
| 4 | tea leaves (20%), lotus leaves (10%), *Galla chinensis* (15%), *Stevia rebaudiana* (10%), *Cyclocarya paliurus* (15%), *Gynura divaricata* (10%), *Taraxacum mongolicum* (10%), *Solanum lycopersicum* (10%) |
| 5 | tea leaves (20%), lotus leaves (10%), extract of *Galla chinensis* (15%), extract of *Stevia rebaudiana* (10%), extract of *Cyclocarya paliurus* (15%), extract of *Gynura divaricata* (10%), extract of *Taraxacum mongolicum* (15%), extract of *Solanum lycopersicum* (5%) |

Embodiment 6

Verification of therapeutic effects on DFUs based on the formulations shown in Table 1 above.

I. Construction of Diabetic Rat Models

1. Experimental Animals:
   (1) Type: specific pathogen free (SPF) grade Sprague Dawley (SD) rats, male, aged 6-8 weeks, weighing 190 grams (g);
   (2) Number: 10 SPF grade SD rats
2. Construction of Diabetic Rat Models:
   (1) A streptozotocin (STZ) solution is prepared and used immediately, and the prepared STZ solution need to be used within 10 minutes;
   (2) The rats are prepared to intraperitoneally inject the STZ solution into the lower left abdomen at a dose of 55 milligrams per kilogram (mg/kg);
   (3) After one week of intraperitoneal injection of the STZ solution, rats are fasted for 12 hours, and then their blood glucose levels are measured. Those with blood glucose levels above 12.6 millimoles per milliliter (mmol/mL) are selected as the diabetic rat model.
3. Construction of Diabetic Rat Models with DFUs A. Modeling with Suspension of *Staphylococcus aureus*

At the third week of the diabetic rat models, 10 microliters (μL) suspension of *Staphylococcus aureus* containing more than $10^6$ of *Staphylococcus aureus* are injected subcutaneously at the dorsal side of the hind foot of the diabetic rat models, thereby causing an animal model of diabetic acral infection. At the third week of successful modeling of the STZ solution induced diabetes in rats, the 10 μL suspension of *Staphylococcus aureus* are injected subcutaneously at the dorsal side of the hind foot of the diabetic rat models (containing more than $10^6$ bacteria), and spontaneous foot gangrenes appear on the $6^{th}$ day, and obvious foot gangrenes appear on the $7-8^{th}$ day. As shown in FIG. 1.

Figure 2:
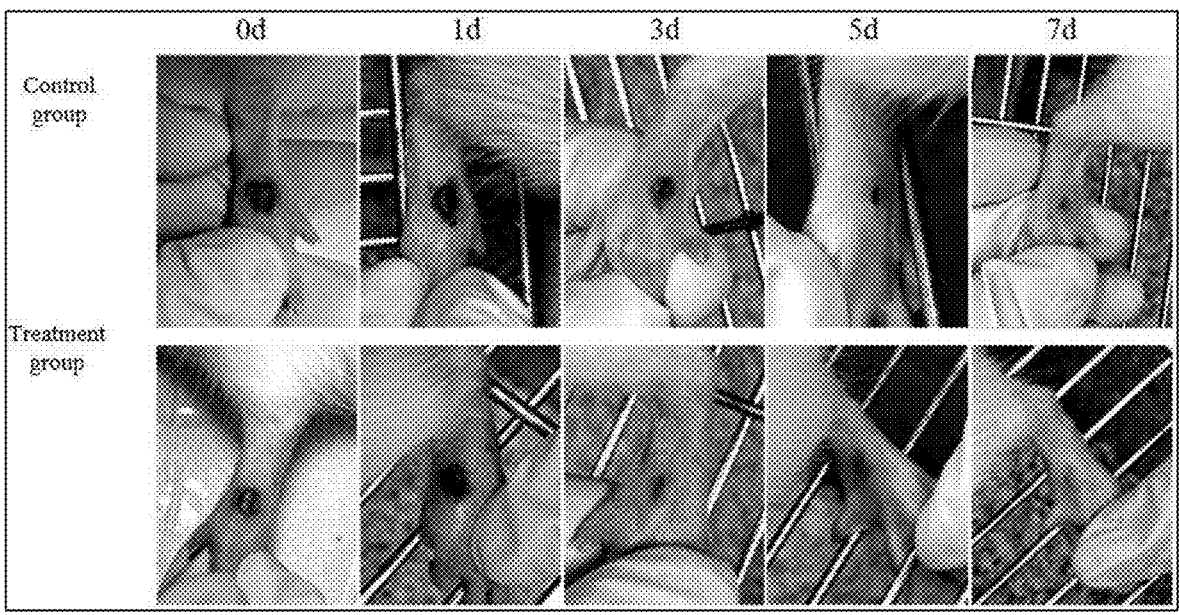
FIG. 2 illustrates a diagram showing therapeutic effects of the rats infected with the *Staphylococcus aureus*.

The rats with foot gangrene are treated using the ratio shown in embodiment 1. The medication regimen is as follows: the gangrene of left hind limb foot is used as a control (without medication treatment), right hind limb is treated with medication (the plant extract), foot gangrene is moistened with physiological saline and topical medication (external application medicine) is applied once a day until the gangrene healed. The results showed that the healing speed of the same area of gangrene is significantly faster when the medicine in embodiment 1 is applied externally than in the control group. The gangrene is healed within 5 days of medicine addition, and in the control group, the gangrene is healed within 7 days. Please refer to FIG. 2 for details.

B. Modeling of Skin Wound of the Rat Treated with Acetic Acid

Figure 3:
FIG. 3 illustrates a modeling diagram of skin wounds of the rats treated with acetic acid ($CH_3COOH$).

At the fourth week successful STZ-induced diabetic modeling in rats, a wound with a diameter of about 5 millimeters (mm) is made on the dorsal side of the hind foot after the diabetic rats in conventional feeding are anesthetized, and 50% glacial acetic acid is used to wipe the wound once a day for one week (as shown in FIG. 3).

Figure 4:
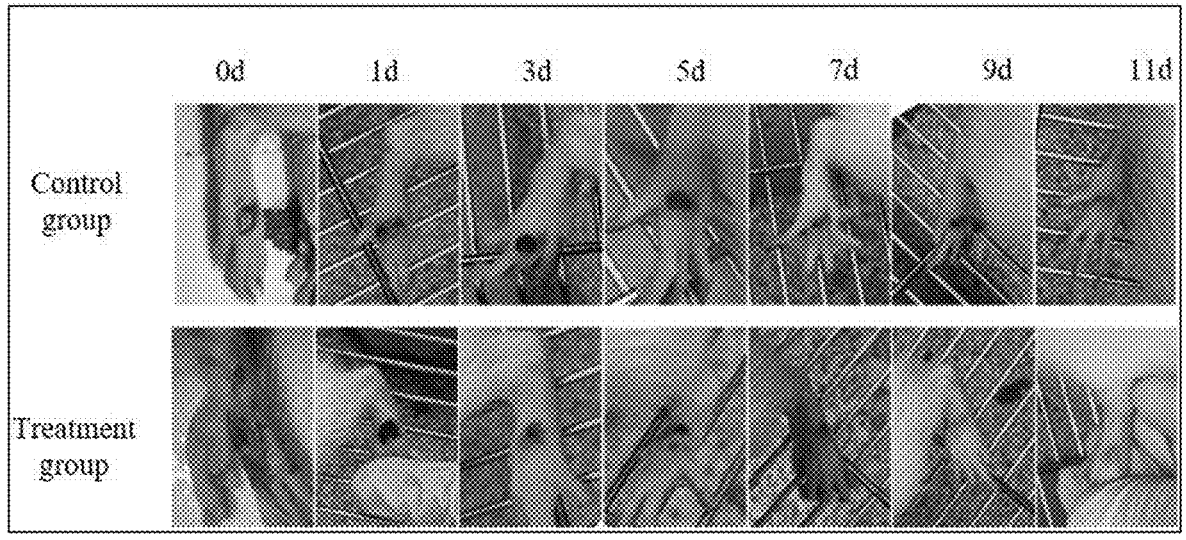
FIG. 4 illustrates a diagram showing therapeutic effects of the skin wounds of the rats treated with the acetic acid.

The rats with foot gangrene are treated using the ratio shown in embodiment 2. The medication regimen is as follows: foot gangrene of left hind limb is used as a control (without medication treatment), right hind limb is treated with medication (the plant extract), foot gangrene is moistened with physiological saline and the topical medication is applied once a day until the gangrene healed. The results showed that the healing speed of the applied foot is similar to that of the control group, and the healing speed of the wound area is faster than that of the control group. Please refer to FIG. 4 for details.

C. Skin Wound Modeling

Figure 5:
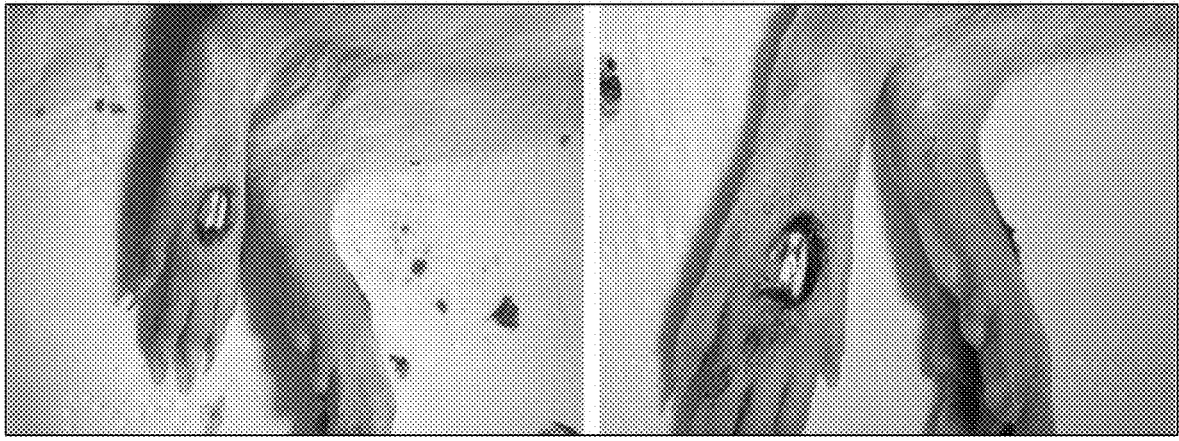
FIG. 5 illustrates a modeling diagram of the skin wounds of the rats.

At the fourth week successful STZ-induced diabetic modeling in rats, a wound with a diameter of about 5 millimeters (mm) is made on the dorsal side of the hind foot after the diabetic rats in conventional feeding are anesthetized, thereby causing foot gangrenes (as shown in FIG. 5).

Figure 6:
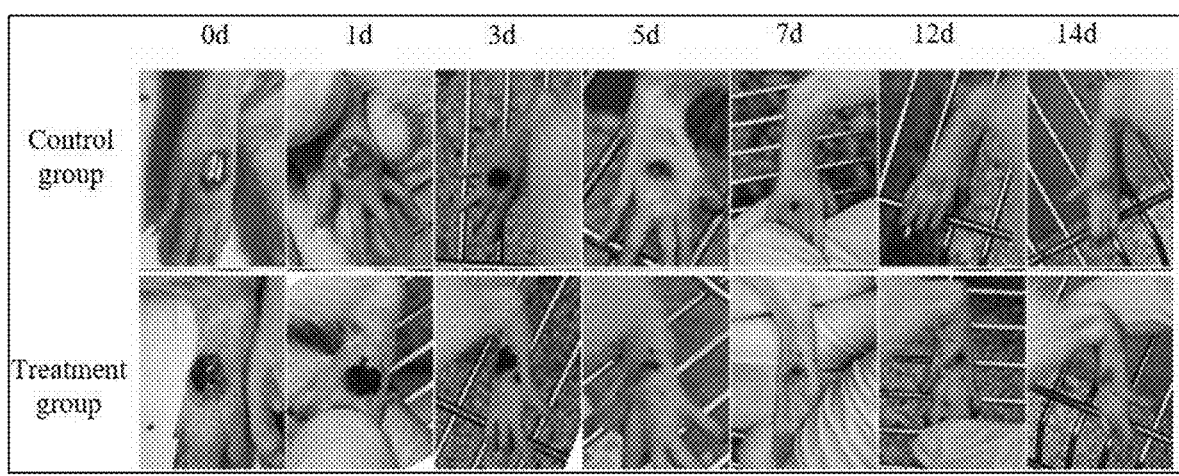
FIG. 6 illustrates a diagram showing therapeutic effects of the skin wounds of the rats.

The rats with foot gangrene are treated using the ratio shown in embodiment 3. The medication regimen is as follows: foot gangrene of left hind limb is used as a control (without medication treatment), right hind limb is treated with medication (the plant extract), foot gangrene is moistened with physiological saline and the topical medication is applied once a day until the gangrene healed. The results showed that the foot healing speed is faster than that of the control group, indicating that the medicine shown in embodiment 3 has a promoting effect on gangrene healing. As shown in FIG. 6.

Embodiment 7

Promotion of Healing of Skin Injury by Plant Extract

1. The grouping of the following experiments is as follows:
   (1) Normal control group with normal feeding (con)
   (2) Skin wound group (wound)
   Establishment of an animal model of skin wound:
   C57BL/6 mice are anesthetized by intraperitoneal injection, shaved on the back and disinfected routinely. On both sides of the midline of the back, with a distance of 1 centimeter (cm) from the midline as the center, a full-thickness circular incision with a diameter of 0.6 cm is made using a trephine to remove the central circular skin. The incision is not bandaged or sutured, naturally healed, and keeps the wound dry. Routine diet is administered.

(3) Skin wound+plant extract treatment group (the plant extract prepared using the ratio shown in embodiment 4).

(4) Skin wound+ointment treatment group

The method of administration is: to apply medicine on the wound once every morning and once every evening.

Specifically, according to parts by weight, the formulation of the ointment of the ointment treatment group is: 5 parts by weight of the plant extract, 5 parts by weight of liquid paraffin, 5 parts by weight of lanolin, and 35 parts by weight of Vaseline, which are mixed together to use. The plant extract is prepared using the ratio shown in embodiment 5.

2. The Effect of Plant Extract on Skin Injury

The time points for detecting wound area are 6, including 0 d, 1 d, 3 d, 5 d, 7 d, and 9 d.

Figure 7:
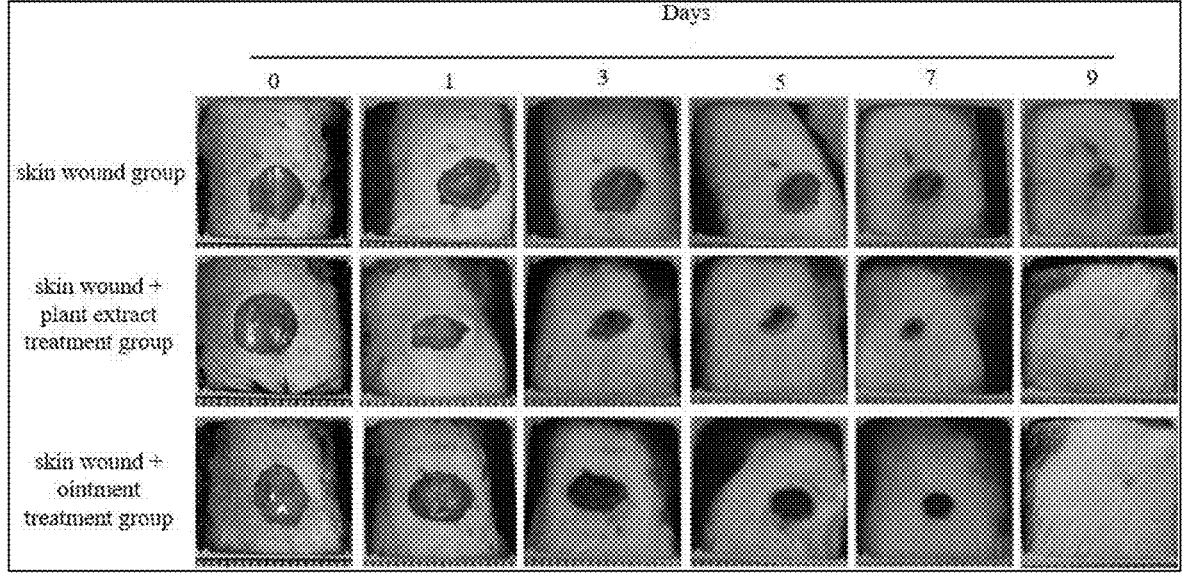
FIG. 7 illustrates a diagram of effects of a plant extract on the skin wounds.

Method: polyester projection film is used to depict the size of the wound surface, and the image information is input into the computer. Image analysis software (Image Pro Plus 6.0, IPP 6.0) is used to analyze the wound area and calculate the wound closure rate. The results are shown in FIG. 7. The results showed that the plant extract effectively promote wound healing.

3. Effects of the plant extract on skin pathology detected by a hematoxylin-eosin (HE) staining experiment, and the process of the detection is as follows.

(1) Paraffin sections of the skin wound are dewaxed to water: the sections of the skin wound are sequentially placed in xylene I for 20 minutes-xylene II for 20 minutes-anhydrous ethanol I for 5 minutes-anhydrous ethanol II for 5 minutes-75% alcohol for 5 minutes, and followed by rinsing the sections of the skin wound with tap water.

(2) Hematoxylin staining: the rinsed sections of the skin wound are stained with hematoxylin staining solution for 3-5 minutes, followed by washing the sections stained hematoxylin with the tap water, and the washed sections stained hematoxylin are differentiated with a differentiation solution, followed by rinsing the differentiated sections with the tap water, then the differentiated sections become blue with a bluing agent, followed by rinsing with the tap water.

(3) Eosin staining: the blued sections are sequentially dehydrated with 85% alcohol and 95% alcohol for 5 minutes, and followed by staining with an eosin staining solution for 5 minutes.

(4) Dehydration and sealing: stained sections are sequentially placed in anhydrous ethanol I (5 minutes)—anhydrous ethanol II (5 minutes)—anhydrous ethanol III (5 minutes)—xylene I (5 minutes)—xylene II (5 minutes) for clearing, and sealed with neutral resin.

(5) Microscopic examination, image acquisition and analysis are performed.

(6) Result interpretation: the nucleus is blue and the cytoplasm is red.

Figure 8:
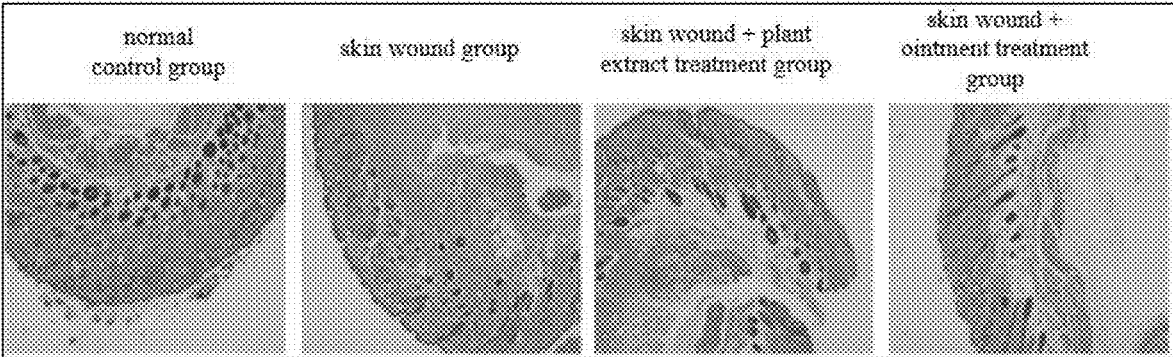
FIG. 8 illustrates a diagram of effects of the plant extract on skin pathology detected by a hematoxylin-eosin (HE) staining experiment.

The results are shown in FIG. 8. The results showed that the plant extract effectively promotes wound healing.

4. Effects of the Plant Extract on Skin Angiogenesis Detected by an Immunofluorescence Assay.

The detection process is as follows: paraffin sections are dewaxed to replace the wax with water, and then the tissue sections are placed in a repair box filled with ethylenedi-aminetetraacetic acid (EDTA) antigen repair buffer (pH 8.0) for antigen repair in a microwave oven, and blocked with 3% bovine albumin (BSA). After adding the primary anti-bodies, the tissue sections are laid in a wet box and incubated at 4° C. overnight. Then the secondary antibodies are added to incubate at the room temperature in the dark for 50 minutes. 4',6-diamidino-2-phenylindole (DAPI) is used to restained the cell nucleus and incubate at the room tempera-ture in dark for 10 minutes. The tissue autofluorescence is quenched, and the sections are slightly shaken dry and sealed with an anti-fluorescence quenching sealing agent. The tissue sections are observed under a fluorescence micro-scope to capture images. Paraffin section immunofluores-cence result interpretation: The nuclei stained with DAPI are blue under the ultraviolet excitation, and positive expression is indicated by the corresponding fluorescence labeled green light map.

Figure 9:
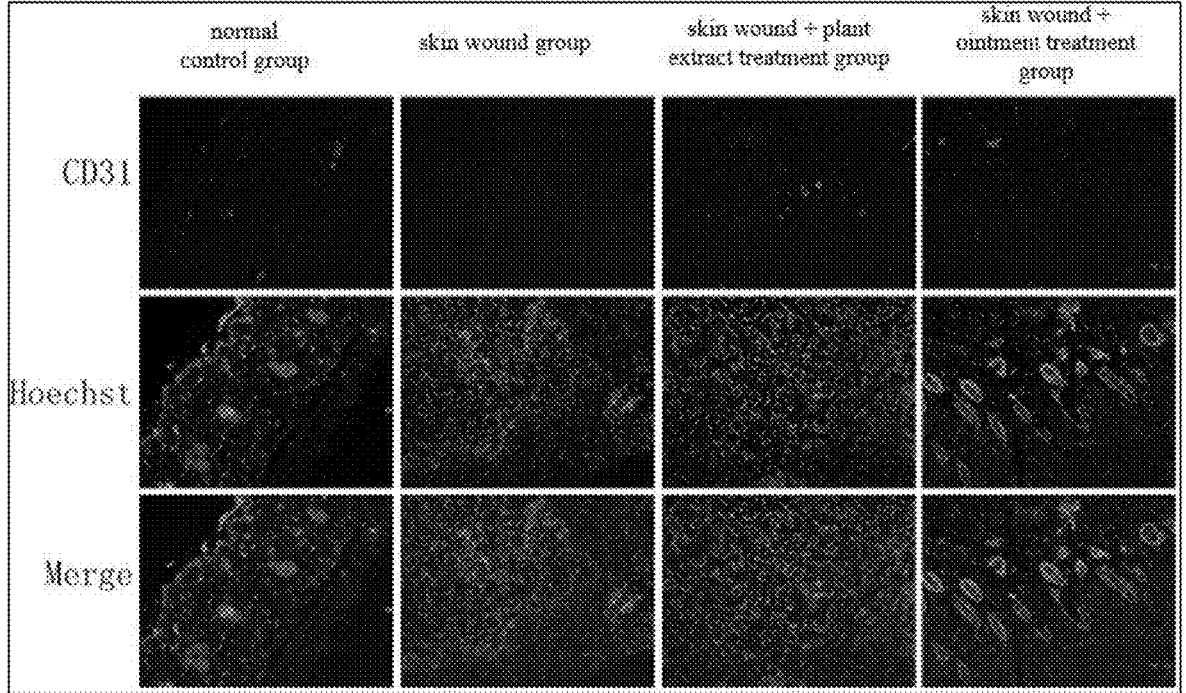
FIG. 9 illustrates a diagram of effects of the plant extract on skin angiogenesis detected by an immunofluorescence assay.

The results are shown in FIG. 9. The plant extract effectively promotes wound angiogenesis, and positive CD31 staining indicates increased angiogenesis.

The above embodiments are only a description of the illustrated embodiments of the disclosure, and do not limit the scope of the disclosure. Without departing from the design spirit of the disclosure, all variations and improve-ments made by those skilled in the art to the technical solution of the disclosure should fall within the scope of protection determined by the claims of the disclosure.

What is claimed is:

1. A preparation method of a plant extract using a plant composition for wound treatment, wherein the plant com-position comprises: tea leaves, lotus leaves, *Galla chinensis, Stevia rebaudiana, Cyclocarya paliurus, Gynura divaricata, Taraxacum mongolicum*, and *Solanum lycopersicum*; and the preparation method comprises:

step (1), crushing a mixture of the tea leaves, the lotus leaves, the *Galla chinensis*, the *Stevia rebaudiana*, the *Cyclocarya paliurus*, the *Gynura divaricata*, the *Taraxacum mongolicum* and the *Solanum lycopersicum* prepared according to a ratio to obtain a crushed mixture, wrapping the crushed mixture in a gauze and adding sodium carbonate ($Na_2CO_3$) to obtain a mixture to be treated, followed by boiling the mixture to be treated with ethanol to collect a first extraction solution, than washing the gauze wrapped with the mixture after the boiling multiple times using the ethanol to obtain a washing solution, and adding the washing solution into the first extraction solution to obtain a first target extraction solution;

step (2), concentrating the first target extraction solution to obtain a concentrated extraction solution, cooling the concentrated extraction solution to a room temperature, performing fluid extraction 1-3 times on the concen-trated extraction solution after cooling with chloroform to obtain a second extraction solution and an aqueous layer, extracting the aqueous layer 1-3 times with ethyl acetate to obtain an extraction solution of the aqueous layer, and combining the second extraction solution and the extraction solution of the aqueous layer to obtain a second target extraction solution; and step (3), distilling the second target extraction solution under a reduced pressure until the second target extrac-tion solution is concentrated to be a solid extract, cooling the solid extract to a room temperature, and freeze-drying the solid extract after cooling to obtain a plant extract in a form of powder.

2. A preparation method of a plant extract using a plant composition for wound treatment, wherein the plant com-position comprises: tea leaves with a mass percentage in a range of 10%-40%, lotus leaves with a mass percentage in a range of 9%-30%, *Galla chinensis* with a mass percentage in a range of 9%-20%, *Stevia rebaudiana* with a mass percentage in a range of 9%-20%, *Cyclocarya paliurus* with a mass percentage in a range of 9%-20%, *Gynura* divaricate with a mass percentage in a range of 9%-20%, *Taraxacum mongolicum* with a mass percentage in a range of 9%-20%, and *Solanum lycopersicum* with a mass percentage in a range of 5%-20%; and the preparation method comprises:

step (1), crushing a mixture of the tea leaves, the lotus leaves, the *Galla chinensis*, the *Stevia rebaudiana*, the *Cyclocarya paliurus*, the *Gynura divaricata*, the *Taraxacum mongolicum* and the *Solanum lycopersicum* prepared according to a ratio to obtain a crushed mixture, wrapping the crushed mixture in a gauze and adding sodium carbonate to obtain a mixture to be treated, followed by boiling the mixture to be treated with ethanol to collect a first extraction solution, than washing the gauze wrapped with the mixture after the boiling multiple times using the ethanol to obtain a washing solution, and adding the washing solution into the first extraction solution to obtain a first target extraction solution;

step (2), concentrating the first target extraction solution to obtain a concentrated extraction solution, cooling the concentrated extraction solution to a room temperature, performing fluid extraction 1-3 times on the concentrated extraction solution after cooling with chloroform to obtain a second extraction solution and an aqueous layer, extracting the aqueous layer 1-3 times with ethyl acetate to obtain an extraction solution of the aqueous layer, and combining the second extraction solution and the extraction solution of the aqueous layer to obtain a second target extraction solution; and step (3), distilling the second target extraction solution under a reduced pressure until the second target extraction solution is concentrated to be a solid extract, cooling the solid extract to a room temperature, and freeze-drying the solid extract after cooling to obtain a plant extract in a form of powder.

3. The preparation method as claimed in claim 1, wherein a mass ratio of the crushed mixture to the sodium carbonate is in a range of 5-10:1-2.

4. The preparation method as claimed in claim 2, wherein a mass ratio of the crushed mixture to the sodium carbonate is in a range of 5-10:1-2.

* * * * *